(12) United States Patent
Farber

(10) Patent No.: US 6,329,413 B1
(45) Date of Patent: Dec. 11, 2001

(54) ALLANTOIN-CONTAINING SKIN CREAM

(75) Inventor: Elliott Farber, North Mankato, MN (US)

(73) Assignee: Alwyn Company, Inc., Lake Crystal, MN (US)

(*) Notice: Subject to any disclaimer, the term of this patent is extended or adjusted under 35 U.S.C. 154(b) by 0 days.

(21) Appl. No.: 09/570,266

(22) Filed: May 12, 2000

Related U.S. Application Data

(63) Continuation-in-part of application No. 09/360,095, filed on Jul. 23, 1999.

(51) Int. Cl.$^7$ ............... A61K 31/415; A61K 31/715; A61K 71/48
(52) U.S. Cl. ............... 514/390; 424/400; 424/401; 424/78.02; 424/78.06; 424/78.18; 514/937; 514/938; 514/939; 514/940; 514/941; 514/943
(58) Field of Search ................... 424/405, 400, 424/401; 514/390, 937, 939, 940, 941, 943, 938

(56) References Cited

U.S. PATENT DOCUMENTS

| | | | |
|---|---|---|---|
| 3,830,824 | 8/1974 | Margraf | 260/299 |
| 3,830,825 | 8/1974 | Margraf | 260/299 |
| 3,830,908 | 8/1974 | Klippel et al. | 424/28 |
| 3,856,805 | 12/1974 | Margraf | 260/299 |
| 3,930,000 | 12/1975 | Margraf | 424/245 |
| 3,932,627 | 1/1976 | Margraf | 424/183 |
| 3,954,989 | 5/1976 | Mecca | 424/273 |
| 4,170,229 | 10/1979 | Olson | 128/67 |
| 4,278,664 | 7/1981 | Van Cleave | 424/148 |
| 4,374,766 | 2/1983 | Puchalski et al. | 260/123.7 |
| 4,670,263 | 6/1987 | Noorlander | 424/195.1 |
| 4,707,354 | 11/1987 | Garlen et al. | 424/47 |
| 4,708,813 | 11/1987 | Snyder | 252/90 |
| 4,806,262 | 2/1989 | Snyder | 252/90 |
| 4,880,621 * | 11/1989 | Grollier et al. | 424/74 |
| 4,981,845 | 1/1991 | Pereira | 514/557 |
| 5,112,886 | 5/1992 | Phalangas | 523/332 |
| 5,122,533 | 6/1992 | Bar-On et al. | 514/390 |
| 5,221,535 | 6/1993 | Perlman | 424/73 |
| 5,455,033 | 10/1995 | Silverman et al. | 424/195 |
| 5,512,200 | 4/1996 | Garcia | 252/142 |
| 5,567,427 | 10/1996 | Papadakis | 424/401 |
| 5,658,559 | 8/1997 | Smith | 424/78.02 |
| 5,661,170 | 8/1997 | Chodosh | 514/390 |
| 5,736,128 | 4/1998 | Chaudhuri et al. | 424/78.03 |
| 5,824,666 | 10/1998 | Deckner et al. | 514/152 |
| 5,827,870 | 10/1998 | Chodosh | 514/390 |
| 5,863,548 | 1/1999 | Elder | 424/408 |
| 5,871,754 | 2/1999 | Briggs et al. | 424/401 |
| 5,876,736 * | 3/1999 | Cohen et al. | 424/401 |
| 5,885,581 | 3/1999 | Massand | 424/195.1 |
| 5,914,116 | 6/1999 | Suares et al. | 424/401 |
| 5,932,228 | 8/1999 | Hall et al. | 424/401 |
| 5,952,373 | 9/1999 | Lanzendörfer et al. | 514/456 |
| 5,958,436 | 9/1999 | Hahn et al. | 424/401 |
| 6,060,061 | 5/2000 | Breton et al. | 424/195.1 |
| 6,080,393 * | 6/2000 | Liu et al. | 424/78.03 |

FOREIGN PATENT DOCUMENTS

| | | | |
|---|---|---|---|
| 030157 | 8/1990 | (EP) | A61K/33/04 |
| 0242553 | 10/1997 | (EP) | A61K/33/04 |
| 1346544 | 2/1974 | (GB) | C07D/49/32 |
| 58140013-A * | 8/1993 | (JP) . | |
| WO 90/09779 | 9/1990 | (WO) | A61K/7/16 |

OTHER PUBLICATIONS

Merck index, pp. 128, 735, 1213, 1996.*
Reminton: the practice of pharmacy 19th edition pp. 639–640, 1995.*
The Complete Illustrated Herbal, Barnes & Nobles pp. 63, 104, 1996.*
publication—product information insert for Alphosyl Cream and Alphosyl Lotion, G.D. Searle (South Africa), Apr. 24, 1975.
publication—product information insert for Clearasil Medicated Facial Cleanser, Procter & Gamble (South Africa), Jan. 31, 1994.
publication—product information insert for Arola Rosebaum, Supramed Limited, Jan. 12,1986.
abstract of a publication—M. Cajkovac et al., "Influence of Emulsoid Vehicle on the Release and Activity of Allantoin," Pharmazie 47: 39–43 (1992).
abstract of a publication—M. Maragakis et al., "Possibilities of Scar Treatment After Thoracic Surgery," Drugs Under Exp. & Clin. Res. 21: P199–206 (1995).
product information insert for Alphosyl, undated.
abstract of a publication—G. Stinco et al., "Seborrheic Dermatitis Treated with Furalglucitole Cream," Dermatol. Clin. 18: 78–81 (1998).
abstract of a publication—M. Maragakis et al., "Possibilities of Scar Treatment After Thoracic Surgery," Drugs Exp. Clin. Res. 21: 199–206 (1999).
abstract of a publication—G.H. Willital & H. Heine, "Efficiency of Contractubex® Gel in the Treatment of Fresh Scars After Thoracic Surgery in Children and Adolescents," Int. J. Clin. Pharmacol. Res. 14: 193–202 (1994).
publication—H.W. Margraf & T.H. Covey, Jr., "A Trial of Silver–Zinc–Allantoinate in the Treatment of Leg Ulcers," Arch. Surg. 12: 699–704 (1977).

* cited by examiner

*Primary Examiner*—Diana Dudash
*Assistant Examiner*—Shahnam Sharareh
(74) *Attorney, Agent, or Firm*—Oppenheimer Wolff & Donnelly LLP

(57) ABSTRACT

An allantoin-containing skin cream composition can comprise allantoin and at least one anionic or nonionic emulsifier that is substantially hydrophilic and is soluble in water. The pH of the composition is in a range of from about 5.0 to about 6.5. The composition can further comprise an acidic anionic polymer. A preferred acidic anionic polymer is a carboxypolymethylene polymer. The composition can further comprise a carbohydrate polymer such as galactoarabinan, polygalactose or polyarabinose. The composition can additionally comprise other ingredients such as herbal extracts, an antioxidant component, an emollient component, a chelator, a solvent component, or a preservative component. The composition is useful as a skin protectant.

34 Claims, No Drawings

ALLANTOIN-CONTAINING SKIN CREAM

CROSS REFERENCES

This application is a continuation-in-part application of application Ser. No. 09/360,095, entitled "Oil-in-Water Emulsion With Improved Stability," filed Jul. 23, 1999 by Elliott Farber, which application is hereby incorporated in its entirety by this reference.

BACKGROUND OF THE INVENTION

This invention is directed to a skin cream containing allantoin in an oil-in-water emulsion with improved stability.

Allantoin is a commonly used ingredient in cosmetic applications, particularly for skin creams, where it exerts a skin protective function. Many such cosmetic compositions and other compositions are prepared as emulsions, particularly oil-in-water emulsions. One emulsifier system used with such compositions is a combination of sodium lauryl sulfate and beeswax. Although solutions of sodium lauryl sulfate are alkaline with an approximate pH of 9.5, the simultaneous use of beeswax with its organic acids produces a complex and neutralized system with a pH of about 6.8 to about 7.5. However, in such a system with a pH range of 6.8 to 7.5, allantoin degrades significantly with time and in accelerated stability tests at 40° C. Because cosmetics and other preparations designed for application to the skin are typically stored by users at room temperature, and room temperatures can fluctuate with climatic conditions, such a degree of stability is undesirable. Therefore, there is a need for an oil-in-water emulsified composition containing allantoin in which the stability of allantoin is increased.

In particular, there is a need for compositions that are suitable for treating a number of severe and difficult-to-treat skin conditions. One of these skin conditions is epidermolysis bullosa. This is a severe genetic skin disorder in which the skin breaks down and large blisters appear. These blisters are difficult to treat by conventional means. Other skin diseases for which improved treatments are needed are pressure ulcers, decubitus ulcers or bed sores, and diabetic ulcers, as well as milia. Therefore, improved compositions that are suitable for treating these diseases are needed.

SUMMARY

In general, a composition according to the present invention comprises an oil-in-water emulsion comprising:

(1) allantoin; and
(2) at least one anionic or nonionic emulsifier that is substantially hydrophilic and is soluble in water.

The pH of the composition is in a range of from about 5.0 to about 6.5. This pH range stabilizes the allantoin and makes storage of the composition for extended periods practical.

Typically, the at least one anionic or nonionic emulsifier is selected from the group consisting of:

(1) an acidic anionic polymer;
(2) an anionic emulsifier selected from the group consisting of sodium lauryl sulfate, sodium laureth sulfate, sodium oleyl succinate, sodium dodecylbenzenesulfonate, and sodium lauryl sarcosinate;
(3) a nonionic emulsifier that is an ethoxylated ether or an ethoxylated ester whose chain length ranges from 8 to 22 carbon atoms;
(4) glyceryl stearate;
(5) cetyl alcohol;
(6) stearic acid;
(7) sodium stearoyl lactylate;
(8) sodium isostearoyl lactylate;
(9) triethanolamine;
(10) a polyethylene glycol ether of cetearyl alcohol wherein the number of olyethylene glycol moieties in the ether is from 6 to 40; and
(11) beeswax.

The composition can further comprise a carbohydrate polymer selected from the group consisting of galactoarabinan, polygalactose, and polyarabinose. Typically, the carbohydrate polymer is galactoarabinan.

One embodiment of the present invention is a composition comprising an oil-in-water emulsion comprising:

(1) allantoin; and
(2) an emulsifier system comprising:
   (a) an acidic anionic polymer; and
   (b) a polyethylene glycol ester of stearic acid.

The pH of the composition is from about 5.0 to about 6.5. Typically, in this embodiment, the acidic anionic polymer is a carboxypolymethylene polymer.

The composition can further comprise a carbohydrate polymer. Typically, the carbohydrate polymer is selected from the group consisting of galactoarabinan, polygalactose, and polyarabinose. Preferably, the carbohydrate polymer is galactoarabinan.

Another embodiment of the present invention is a composition comprising an oil-in-water emulsion comprising:

(1) allantoin; and
(2) an emulsifier system comprising:
   (a) an acidic anionic polymer; and
   (b) an anionic emulsifier that is substantially hydrophilic and is soluble in water, the pH of the composition being adjusted to a range of from about 5.0 to about 6.5.

The anionic emulsifier can be selected from the group consisting of sodium lauryl sulfate, sodium laureth sulfate, sodium oleyl succinate, sodium dodecylbenzenesulfonate, and sodium lauryl sarcosinate. Preferably, the anionic emulsifier is sodium lauryl sulfate.

The composition can further comprise a carbohydrate polymer selected from the group consisting of galactoarabinan, polygalactose and polyarabinose. Preferably, the carbohydrate polymer is galactoarabinan.

Another embodiment of the present invention is a composition comprising an oil-in-water emulsion comprising:

(1) allantoin;
(2) an emulsifier system comprising an acidic anionic polymer; and
(3) a base to adjust the pH of the composition to a value in a range from about 5.0 to about 5.5.

Preferably, the acidic anionic polymer is a carboxypolymethylene polymer. Preferably, the base is an organic base such as triethanolamine.

In another embodiment, the composition comprises an oil-in-water emulsion comprising:

(1) allantoin;
(2) an emulsifier system comprising:
   (a) an acidic anionic polymer; and
   (b) a nonionic emulsifier that is an ethoxylated ether or an ethoxylated ester whose carbon chain length ranges from 8 to 22 carbon atoms, wherein the pH of the composition is from about 5.0 to about 6.5.

In this embodiment, the emulsifier system can further comprise glyceryl stearate.

This embodiment also can include a carbohydrate polymer as described above.

In yet another embodiment of the present invention, a composition comprising an oil-in-water emulsion comprising:

(1) allantoin;
(2) an emulsifier system comprising:
   (a) sodium stearoyl lactylate;
   (b) sodium isostearoyl lactylate;
   (c) optionally, triethanolamine;
   (d) optionally, at least one nonionic emulsifier selected from the group consisting of a nonionic emulsifier that is an ethoxylated ether or an ethoxylated ester whose carbon chain length ranges from 8 to 22 carbon atoms; and
(3) an acid to adjust the pH to a range of from about 5.0 to about 5.8.

Typically, the acid is citric acid.

Still another embodiment of the present invention is a composition comprising an oil-in-water emulsion comprising:

(1) allantoin; and
(2) an emulsifier system comprising at least one polyethyleneglycol ether of cetearyl alcohol, wherein the number of polyethylene glycol moieties in the polyethyleneglycol ether of cetearyl alcohol is from 6 to 40; and
(3) an acid to adjust the pH of the composition to a range of from about 5.0 to about 5.8.

For this embodiment, the acid is typically also citric acid.

For this embodiment, the emulsifier system typically comprises ceteareth-25 and ceteareth-6.

Yet another embodiment of the present invention is a composition comprising an oil-in-water emulsion comprising:

(1) allantoin;
(2) an emulsifier system comprising:
   (a) a polyethylene glycol ester of stearic acid; and
   (b) glyceryl stearate; and
(3) an acid to adjust the pH of the composition to a range of from about 5.0 to about 5.8.

Typically, in this embodiment, the number of ethylene glycol moieties in the polyethylene glycol ester of stearic acid is from 25 to 100. Preferably, the polyethylene glycol ester of stearic acid is PEG-100 stearate. Typically, in this embodiment, the acid is citric acid.

Still another embodiment of the present invention is a composition comprising an oil-in-water emulsion comprising:

(1) allantoin;
(2) a carbohydrate polymer; and
(3) an emulsifier system comprising:
   (a) beeswax; and
   (b) an anionic emulsifier that is substantially hydrophilic and is soluble in water;
wherein the pH of the composition is in a range from about 5.0 to about 6.5.

The carbohydrate polymer in this embodiment is as described above.

Typically, the anionic emulsifier that is substantially hydrophilic and soluble in water is selected from the group consisting of sodium lauryl sulfate, sodium laureth sulfate, sodium oleyl succinate, sodium dodecylbenzenesulfonate, and sodium lauryl sarcosinate. Preferably, the anionic emulsifier is sodium lauryl sulfate.

The composition can further comprise citric acid to adjust the pH.

For all of these embodiments, the composition can comprise one or more additional ingredients as described below.

The composition can comprise an emollient component comprising at least one emollient selected from the group consisting of lanolin oil, cetyl alcohol, stearyl alcohol, and cod liver oil.

The composition can comprise an emollient such as butylated hydroxytoluene.

The composition can comprise herbal extracts such as one or more of St. John's wort extract, witch hazel extract, chamomile extract, and arnica extract.

The composition can comprise a preservative component comprising at least one preservative selected from the group consisting of methylparaben, propylparaben, and diazolidinyl urea.

The composition can comprise a chelating agent such as tetrasodium EDTA.

The composition can comprise a solvent component comprising at least one solvent selected from the group consisting of propylene glycol, butylene glycol and glycerin. Preferably, the solvent component is propylene glycol.

Ranges of compositions are disclosed for each of these embodiments.

DESCRIPTION

A composition according to the present invention comprises an oil-in-water emulsion comprising:

(1) allantoin; and
(2) at least one anionic or nonionic emulsifier that is substantially hydrophilic and is soluble in water.

The pH of the composition is in a range of from about 5.0 to about 6.5. This pH range stabilizes the allantoin and makes storage of the composition for extended periods practical.

Typically, the at least one anionic or nonionic emulsifier is selected from the group consisting of:

(1) an acidic anionic polymer;
(2) an anionic emulsifier selected from the group consisting of sodium lauryl sulfate, sodium laureth sulfate, sodium oleyl succinate, sodium dodecylbenzenesulfonate, and sodium lauryl sarcosinate;
(3) an nonionic emulsifier that is an ethoxylated ether or an ethoxylated ester whose chain length ranges from 8 to 22 carbon atoms;
(4) glyceryl stearate;
(5) cetyl alcohol;
(6) stearic acid;
(7) sodium stearoyl lactylate;
(8) sodium isostearoyl lactylate;
(9) triethanolamine;
(10) a polyethylene glycol ether of cetearyl alcohol wherein the number of polyethylene glycol moieties in the ether is from 6 to 40; and
(11) beeswax.

The composition can further comprise a carbohydrate polymer selected from the group consisting of galactoarabinan, polygalactose, and polyarabinose. Typically, the carbohydrate polymer is galactoarabinan.

One embodiment of an improved composition containing allantoin is a composition that comprises an oil-in-water emulsion comprising:

(1) allantoin; and
(2) an emulsifier system comprising:
   (a) an acidic anionic polymer; and
   (b) a polyethylene glycol ester of stearic acid.

The pH of the composition is adjusted to a range of from about 5.0 to about 6.5. The pH is adjusted with sodium hydroxide or other base as required.

The acidic anionic polymer is preferably a carboxypolymethylene polymer. Such polymers are marketed under the brand names "Carbomer" and "Carbopol." A suitable carboxypolymethylene polymer is marketed by B. F. Goodrich under the brand name "Carbomer." This is a slightly cross-linked polyacrylic acid that is from 1% to 2% cross-linked by allylsucrose or allylpentaerythritol with the polyacrylic acid. The resulting molecular weight range of this polymer is from about $2 \times 10^6$ daltons to about $1 \times 10^9$ daltons. The average molecular weight of this polymer is about $4 \times 10^6$ daltons.

Preferably, the concentration of the carboxypolymethylene polymer is from about 0.5 percent to about 2 percent of the composition.

The composition can further comprise a carbohydrate polymer. Preferably, the carbohydrate polymer is galactoarabinan. Galactoarabinan is derived from trees of the genus Larix (larch) and is a hemicellulosic product easily extractable by water in a pure form. Galactoarabinan has been consumed by humans in common foods such as carrots, tomatoes, maple syrup, soybeans, and wheat flour, among others. The molecular weight of the galactoarabinan is about 20,000. A suitable source of galactoarabinan is Larex, Inc (White Bear Lake, Minn.). Typically, the composition contains from about 1 percent to about 25 percent of galactoarabinan. Preferably, the composition contains from about 2 percent to about 10 percent of the carbohydrate polymer.

This embodiment of a composition according to the present invention can further include other ingredients. For example, the composition can include an emollient component for smoothness. The emollient component can include at least one emollient selected from the group consisting of lanolin oil, cetyl alcohol, stearyl alcohol, and cod liver oil.

The composition can also include an antioxidant to prevent rancidity of ingredients such as cod liver oil. A preferred antioxidant is butylated hydroxytoluene (BHT).

The composition can further include a solvent component. Typically, the solvent component can include at least one solvent selected from the group consisting of propylene glycol, glycerin, or butylene glycol. Preferably, the solvent component is propylene glycol.

The composition can further include a preservative component. The preservative component can comprise at least one preservative selected from the group consisting of methylparaben, propylparaben, and diazolidinyl urea. Preferably, the preservative component comprises methylparaben, propylparaben, and diazolidinyl urea.

The composition can further include fragrance. The use of fragrance is well known in the cosmetic art and in the art of over-the-counter drug formulation, and many suitable fragrances are known in the art. The stability and function of the cream is not altered by the presence or absence of fragrance.

Optionally, this embodiment of the composition can further include herbal extracts. The herbal extracts can include one or more of St. John's wort extract, witch hazel extract, chamomile extract, and arnica extract. However, these herbal extracts are typically omitted in this embodiment.

This embodiment of the composition can optionally further include other components, such as proteins, humectants, other preservatives, essential oils, other vitamins, colorants, hydroxyacids, other plant extracts, chelators, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 60.0% to about 85.0% of this embodiment of the composition. An optimum concentration of water in this embodiment of the composition is about 69.95%.

The carboxypolymethylene polymer can comprise from about 0.30% to about 3.0% of this embodiment of the composition. Preferably, the carboxypolymethylene polymer comprises from about 0.50% to about 2.0% of this embodiment of the composition. An optimum concentration of the carboxypolymethylene polymer is about 0.85% of this embodiment of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

PEG-100 stearate can comprise from about 0.25% to about 2.5% of this embodiment of the composition. Preferably, PEG-100 stearate comprises from about 0.50% to about 2.0% of this embodiment of the composition. An optimum concentration of PEG-100 stearate is about 1.50% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 8.0% of this embodiment of the composition. A preferred concentration of cetyl alcohol is from about 2.0% to about 7.0% of this embodiment of the composition. An optimum concentration of cetyl alcohol is about 4.20% of this embodiment of the composition.

Stearyl alcohol can comprise from about 0.5% to about 6.0% of this embodiment of the composition. A preferred concentration of stearyl alcohol is from about 0.75% to about 5.0% of this embodiment of the composition. An optimum concentration of stearyl alcohol is about 1.50% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. A preferred concentration of methylparaben is from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.25% of this embodiment of the composition. Preferably, diazolidinyl urea comprises from about 0.10% to about 0.20% of this embodiment of the composition. An optimum concentration of diazolidinyl urea is about 0.15% of this embodiment of the composition.

Allantoin can comprise from about 0.50% to about 2.0% of this embodiment of the composition. A preferred concentration of allantoin is from about 1.0% to about 2.0% of this embodiment of the composition. An optimum concentration of allantoin is about 1.50% of this embodiment of the composition.

Fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of the composition. As indicated above, fragrance can be omitted, and it may be desirable to omit fragrance in circumstances in which the composition is intended for use on sensitive individuals or individuals who may undergo an allergic reaction to fragrance.

Triethanolamine can comprise from about 0.05% to about 3.0% of this embodiment of the composition to adjust the pH. A preferred concentration of triethanolamine is from about 0.20% to about 2.0% of this embodiment of the composition. An optimum concentration of triethanolamine is about 0.80% of this embodiment of the composition.

In another alternative embodiment of the composition, the emulsifier can be an anionic emulsifier that is substantially hydrophilic and is soluble in water. In this embodiment, the anionic emulsifier replaces the polyethylene glycol ester of stearic acid. This embodiment further includes the acidic anionic polymer such as carboxypolymethylene. Optionally, but preferably, this alternative embodiment of the composition includes the carbohydrate polymer such as galactoarabinan.

The anionic emulsifier that is substantially hydrophilic and soluble in water can be selected from the group consisting of sodium lauryl sulfate, sodium laureth sulfate, sodium oleyl succinate, sodium dodecylbenzenesulfonate, and sodium lauryl sarcosinate. A particularly preferred anionic emulsifier is sodium lauryl sulfate.

Commercially available preparations of sodium lauryl sulfate contain sufficient excess sodium hydroxide so that they have a pH of about 10.0. This sodium hydroxide can be used to adjust the pH when the anionic emulsifier is sodium lauryl sulfate; in this alternative, no additional alkali may be needed. When another anionic emulsifier is used, additional alkali may be required to adjust the pH.

In yet another alternative embodiment of the composition, the emulsifier system comprises the acidic anionic polymer as described above and a nonionic emulsifier that is an ethoxylated ether or an ethoxylated ester whose carbon chain length ranges from 8 to 22 carbon atoms.

Preferably, the acidic anionic polymer is carboxypolymethylene as described above.

This alternative embodiment of the composition can further include glyceryl stearate in the emulsifier system.

This embodiment of the composition has a pH from about 5.0 to 6.5, adjusted as necessary, typically with an acid. The acid can be an organic acid, an inorganic acid, or a mixture of both.

This embodiment of the composition can further comprise a carbohydrate polymer such as galactoarabinan as described above.

In this embodiment of the composition, preferred organic acids include organic acids whose carbon chain length ranges from 2 to 22 carbon atoms and can be monocarboxylic, dicarboxylic, or tricarboxylic acids. The acids can be aliphatic or aromatic. Particularly preferred organic acids include citric acid, ascorbic acid, glycolic acid, lactic acid, benzoic acid, and salicylic acid. A most particularly preferred organic acid is citric acid.

Typically, in this embodiment of the composition, the inorganic acid is a strong acid. It can be a monoprotic, diprotic, or triprotic acid. Particularly preferred inorganic acids include hydrochloric acid, sulfuric acid, and phosphoric acid.

This alternative embodiment of the composition can further include other ingredients as described above, including an emollient component, an antioxidant, a solvent component, a chelating agent, herbal extracts, a preservative, and fragrance.

The composition can further include other components, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

In yet another embodiment of the composition, the emulsifier system comprises the acidic anionic polymer described above; one example of this acidic anionic polymer is marketed as Carbomer. In this embodiment, the pH is adjusted with an organic or inorganic base to a range of from about 5.0 to about 5.5. A preferred organic base is triethanolamine. A preferred inorganic base is sodium hydroxide. In general, it is preferred to use an organic base such as triethanolamine.

This embodiment can further comprise other ingredients. For example, this embodiment of the invention can further comprise a solvent component. Typically, the solvent component comprises at least one solvent selected from the group consisting of propylene glycol, glycerin, or butylene glycol. Preferably, the solvent component is propylene glycol.

This embodiment of the invention can further comprise an emollient component. The emollient component can comprise at least one solvent selected from the group consisting of lanolin oil, cetyl alcohol, and cod liver oil. Preferably, the emollient component comprises all of lanolin oil, cetyl alcohol, and cod liver oil.

This embodiment of the composition can also include an antioxidant. A preferred antioxidant is butylated hydroxytoluene.

This embodiment of the invention can further comprise a preservative component. The preservative component can comprise at least one preservative selected from the group consisting of methylparaben and propylparaben. Preferably, the preservative component comprises both methylparaben and propylparaben.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 60.0% to about 80.0% of this embodiment of the composition. An optimum concentration of water is about 73.55% of this embodiment of the composition.

The carboxypolymethylene polymer can comprise from about 0.40% to about 3.0% of this embodiment of the composition. Preferably, the carboxypolymethylene polymer comprises from about 0.5% to about 2.0% of this embodiment of the composition. An optimum concentration of the carboxypolymethylene polymer is about 1.00% of the composition Propylene glycol can comprise from about 2.0% to about 9.0% of this embodiment of the composition. Preferably, the propylene glycol comprises from about 4.0% to about 7.0% of this embodiment of the composition. An optimum concentration of the propylene glycol is about 5.70% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.0% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 3.00% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.30% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Allantoin can comprise from about 0.50% to about 2.0% of this embodiment of the composition. Preferably, allantoin comprises from about 1.0% to about 2.0% of this embodiment of the composition. An optimum concentration of allantoin is about 1.50% of this embodiment of the composition.

Fragrance, if present, can comprise from about 0.05% to about 0.50% of this embodiment of the composition. Preferably, if present, fragrance comprises from about 0.10% to about 0.40% of this embodiment of the composition. An optimum concentration of fragrance, if present, is about 0.20% of this embodiment of the composition.

Triethanolamine, as a 95% solution, can comprise from about 0.05% to about 3.0% of this embodiment of the composition to adjust the pH to a value in the range of from about 5.0 to about 5.5. Preferably, triethanolamine comprises from about 0.20% to about 2.0% of this embodiment of the composition to adjust the pH as indicated. An optimum concentration of triethanolamine is about 0.80% of the composition to adjust the pH as indicated.

Yet another embodiment of a composition according to the present invention is a composition comprising an oil-in-water emulsion comprising:
 (1) allantoin; and
 (2) an emulsifier system comprising:
  (a) cetyl alcohol; and
  (b) stearic acid.

In this embodiment, the pH is adjusted to a range of from about 5.0 to about 5.8 by addition of a quantity of a weak organic base. The weak organic base can be an amine-containing base such as ethanolamine, diethanolamine, or triethanolamine. A preferred organic base is triethanolamine.

This embodiment can further comprise other ingredients. For example, this embodiment of the invention can further comprise a solvent component. Typically, the solvent component comprises at least one solvent selected from the group consisting of propylene glycol, glycerin, or butylene glycol. Preferably, the solvent component is propylene glycol.

This embodiment of the invention can further comprise an emollient component. The emollient component can comprise at least one solvent selected from the group consisting of lanolin oil, cetyl alcohol, and cod liver oil. Preferably, the emollient component comprises all of lanolin oil, cetyl alcohol, and cod liver oil.

This embodiment of the composition can also include an antioxidant. A preferred antioxidant is butylated hydroxytoluene.

This embodiment of the invention can further comprise a preservative component. The preservative component can comprise at least one preservative selected from the group consisting of methylparaben and propylparaben. Preferably, the preservative component comprises both methylparaben and propylparaben.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 60.0% to about 85.0% of this embodiment of the composition. An optimum concentration of water is about 71.70% of this embodiment of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Triethanolamine can comprise from about 0.2% to about 4.0% of this embodiment of the composition. Preferably, triethanolamine comprises from about 0.5% to about 3.0% of this embodiment of the composition. An optimum concentration of triethanolamine is about 1.25% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 7.0% of this embodiment of the composition. Preferably, cetyl alcohol comprises from about 2.0% to about 6.0% of this embodiment of the composition. An optimum concentration of cetyl alcohol is about 3.50% of this embodiment of the composition.

Stearic acid can comprise from about 0.50% to about 5.0% of this embodiment of the composition. Preferably, stearic acid comprises from about 1.0% to about 4.0% of this embodiment of the composition. An optimum concentration of stearic acid is about 2.50% of this embodiment of the composition.

Cod liver oil can comprise from about 1.0% to about 7.0% of this embodiment of the composition. Preferably, cod liver oil comprises from about 1.50% to about 5.0% of this embodiment of the composition. An optimum concentration of cod liver oil is about 2.0% of this embodiment of the composition.

Butylated hydroxytoluene can comprise from about 0.1% to about 1.0% of this embodiment of the composition. Preferably, butylated hydroxytoluene comprises from about 0.2% to about 0.8% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of the composition. An optimum concentration of propylparaben is about 0.25% of this embodiment of the composition.

Allantoin can comprise from about 0.50% to about 2.0% of this embodiment of the composition. Preferably, allantoin comprises from about 1.0% to about 2.0% of this embodiment of the composition. An optimum concentration of allantoin is about 1.50% of this embodiment of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Still another embodiment of a composition according to the present invention is a composition comprising an oil-in-water emulsion comprising:

(1) allantoin; and
(2) an emulsifier system comprising:
  (a) sodium stearoyl lactylate;
  (b) sodium isostearoyl lactylate;
  (c) optionally, triethanolamine;
  (d) optionally, at least one nonionic emulsifier selected from the group consisting of a nonionic emulsifier that is an ethoxylated ether or an ethoxylated ester whose carbon chain length ranges from 8 to 22 carbon atoms.

Sodium stearoyl lactylate is the sodium salt of the stearic acid ester of lactyl lactate. Sodium isostearoyl lactylate is the sodium salt of the isostearic acid ester of lactyl lactate.

In this embodiment of the composition, the composition further comprises an acid to adjust the pH to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of propylene glycol, glycerin, or butylene glycol. Preferably, the solvent component is propylene glycol.

This embodiment of the invention can further comprise an emollient component. The emollient component can comprise at least one emollient selected from the group consisting of lanolin oil, cetyl alcohol, and cod liver oil. Preferably, the emollient component comprises all of lanolin oil, cetyl alcohol, and cod liver oil.

This embodiment of the invention can further comprise a chelator component. Preferably, the chelator component is tetrasodium ethylenediaminetetraacetic acid.

This embodiment of the invention can further comprise a preservative component. The preservative component can comprise at least one preservative selected from the group consisting of methylparaben and propylparaben. Preferably, the preservative component comprises both methylparaben and propylparaben.

This embodiment of the composition can also include an antioxidant. A preferred antioxidant is butylated hydroxytoluene.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 60.0% to about 80.0% of this embodiment of the composition. An optimum concentration of water is about 73.72% of this embodiment of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Citric acid can comprise from about 0.05% to about 0.50% of this embodiment of the composition. Preferably, citric acid comprises from about 0.10% to about 0.40% of this embodiment of the composition. An optimum concentration of citric acid is about 0.18% of this embodiment of the composition.

Sodium stearoyl lactylate can comprise from about 0.30% to about 3.0% of this embodiment of the composition.

Preferably, sodium stearoyl lactylate comprises from about 0.50% to about 2.50% of this embodiment of the composition. An optimum concentration of sodium stearoyl lactylate is about 1.00% of this embodiment of the composition.

Sodium isostearoyl lactylate can comprise from about 0.05% to about 1.0% of this embodiment of the composition. Preferably, sodium isostearoyl lactylate comprises from about 0.10% to about 0.70% of this embodiment of the composition. An optimum concentration of sodium isostearoyl lactylate is about 0.25% of this embodiment of the composition.

Tetrasodium EDTA can comprise from about 0.05% to about 0.25% of this embodiment of the composition. Preferably, tetrasodium EDTA comprises from about 0.10% to about 0.20% of this embodiment of the composition. An optimum concentration of tetrasodium EDTA is about 0.15% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 3.80% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.0% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of the composition. An optimum concentration of propylparaben is about 0.25% of this embodiment of the composition.

Allantoin can comprise from about 0.50% to about 2.0% of this embodiment of the composition. Preferably, allantoin comprises from about 1.0% to about 2.0% of this embodiment of the composition. An optimum concentration of allantoin is about 1.50% of this embodiment of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Still another embodiment of a composition according to the present invention is a composition comprising an oil-in-water emulsion comprising:
(1) allantoin; and
(2) an emulsifier system comprising at least one polyethyleneglycol ether of cetearyl alcohol.

In polyethylene glycol ethers of cetearyl alcohol suitable for use in compositions according to the present invention, the number of ethylene glycol moieties can range from 6 to 40, e.g., $R(OCH_2CH_2)_{25}OH$ where $R=CH_3(CH_2)_{16-18}$. In one preferred embodiment of the present invention, the emulsifier system comprises both ceteareth-25 and ceteareth-6, i.e., polyethylene glycol ethers of cetearyl alcohol with 25 and 6 ethylene glycol units respectively.

In this embodiment of the composition, the composition further comprises an acid to adjust the pH to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

This embodiment of the composition can also include an antioxidant. A preferred antioxidant is butylated hydroxytoluene.

This embodiment of the invention can further comprise a preservative component. The preservative component can comprise at least one preservative selected from the group consisting of methylparaben, propylparaben, and diazolidinyl urea. Preferably, the preservative component comprises all of methylparaben, propylparaben, and diazolidinyl urea.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 55.0% to about 75.0% of this embodiment of the composition. An optimum concentration of water is about 66.33% of this embodiment of the composition.

Propylene glycol can comprise from about 2.0% to about 9.0% of this embodiment of the composition. Preferably, propylene glycol comprises from about 4.2% to about 7.0% of this embodiment of the composition. An optimum concentration of propylene glycol is about 5.70% of this embodiment of the composition.

Tetrasodium EDTA can comprise from about 0.05% to about 0.50% of this embodiment of the composition. Preferably, tetrasodium EDTA comprises from about 0.10% to about 0.30% of this embodiment of the composition. An optimum concentration of tetrasodium EDTA is about 0.15% of this embodiment of the composition.

Ceteareth-25 can comprise from about 0.50% to about 4.0% of this embodiment of the composition. Preferably, ceteareth-25 comprises from about 2.0% to about 3.5% of this embodiment of the composition. An optimum concentration of ceteareth-25 is about 2.60% of this embodiment of the composition.

Citric acid can comprise from about 0.04% to about 0.40% of this embodiment of the composition. Preferably, citric acid comprises from about 0.10% to about 0.30% of this embodiment of the composition. An optimum concentration of citric acid is about 0.12% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 3.0% to about 10.0% of this embodiment of the composition. Preferably, cetyl alcohol comprises from about 3.5% to about 7.5% of this embodiment of the composition. An optimum concentration of cetyl alcohol is about 4.30% of this embodiment of the composition.

Stearyl alcohol can comprise from about 1.0% to about 5.0% of this embodiment of the composition. Preferably, stearyl alcohol comprises from about 2.0% to about 4.0% of this embodiment of the composition. An optimum concentration of stearyl alcohol is about 3.50% of this embodiment of the composition.

Ceteareth-6 can comprise from about 0.5% to about 4.0% of this embodiment of the composition. Preferably, ceteareth-6 comprises from about 1.0% to about 3.0% of this embodiment of the composition. An optimum concentration of ceteareth-6 is about 1.80% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.50% of this embodiment of the composition. Preferably, diazolidinyl urea comprises from about 0.10% to about 0.30% of this embodiment of the composition. An optimum concentration of diazolidinyl urea is about 0.15% of this embodiment of the composition.

Allantoin can comprise from about 0.50% to about 2.0% of this embodiment of the composition. Preferably, allantoin comprises from about 1.0% to about 2.0% of this embodiment of the composition. An optimum concentration of allantoin is about 1.50% of this embodiment of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Yet another embodiment of a composition according to the present invention is a composition comprising an oil-in-water emulsion comprising:

(1) allantoin; and
(2) an emulsifier system comprising:
   (a) a polyethylene glycol ester of stearic acid; and
   (b) glyceryl stearate.

Typically, the number of ethylene glycol moieties in the polyethylene glycol ester of stearic acid is from 25 to 100. Two preferred polyethylene glycol esters of stearic acid for use in this embodiment of compositions according to the present invention are PEG-40 stearate and PEG-100 stearate, with 40 and 100 ethylene glycol moieties respectively. A particularly preferred polyethylene glycol ester of stearic acid is PEG-100 stearate.

In this embodiment of the composition, the composition further comprises an acid to adjust the pH to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component is one or more of propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

This embodiment of the composition can also include an antioxidant. A preferred antioxidant is butylated hydroxytoluene.

This embodiment of the invention can further comprise a preservative component. The preservative component can comprise at least one preservative selected from the group consisting of methylparaben, propylparaben, and diazolidinyl urea. Preferably, the preservative component comprises all of methylparaben, propylparaben, and diazolidinyl urea.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 55.0% to about 80.0% of this embodiment of the composition. An optimum concentration of water is about 67.86% of this embodiment of the composition.

Propylene glycol can comprise from about 2.0% to about 9.0% of this embodiment of the composition. Preferably, propylene glycol comprises from about 4.30% to about 7.00% of this embodiment of the composition. An optimum concentration of propylene glycol is about 5.70% of this embodiment of the composition.

Tetrasodium EDTA can comprise from about 0.05% to about 0.50% of this embodiment of the composition. Preferably, tetrasodium EDTA comprises from about 0.10% to about 0.30% of this embodiment of the composition. An optimum concentration of tetrasodium EDTA is about 0.15% of this embodiment of the composition.

Citric acid can comprise from about 0.04% to about 0.40% of this embodiment of the composition. Preferably, citric acid comprises from about 0.10% to about 0.30% of this embodiment of the composition. An optimum concentration of citric acid is about 0.14% of this embodiment of the composition.

PEG-100 stearate can comprise from about 1.0% to about 5.0% of this embodiment of the composition. Preferably, PEG-100 stearate comprises from about 1.50% to about 3.00% of this embodiment of the composition. An optimum concentration of PEG-100 stearate is about 2.60% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 2.0% to about 10.0% of this embodiment of the composition. Preferably, cetyl alcohol comprises from about 2.50% to about 7.50% of this embodiment of the composition. An optimum concentration of cetyl alcohol is about 3.00% of this embodiment of the composition.

Stearyl alcohol can comprise from about 1.0% to about 4.0% of this embodiment of the composition. Preferably, stearyl alcohol comprises from about 1.0% to about 3.5% of this embodiment of the composition. An optimum concentration of stearyl alcohol is about 2.50% of this embodiment of the composition.

Glyceryl stearate can comprise from about 1.0% to about 5.0% of this embodiment of the composition. Preferably, glyceryl stearate comprises from about 2.0% to about 4.0% of this embodiment of the composition. An optimum concentration of glyceryl stearate is about 2.50% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.50% of this embodiment of the composition. Preferably, diazolidinyl urea comprises from about 0.10% to about 0.30% of this embodiment of the composition. An optimum concentration of diazolidinyl urea is about 0.20% of this embodiment of the composition.

Allantoin can comprise from about 0.50% to about 2.0% of this embodiment of the composition. Preferably, allantoin comprises from about 1.0% to about 2.0% of this embodiment of the composition. A preferred concentration of allantoin is about 1.50% of this embodiment of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Yet another embodiment of a composition according to the present invention is a composition comprising an oil-in-water emulsion comprising:

(1) allantoin;
(2) a carbohydrate polymer; and
(3) an emulsifier system comprising:
   (a) beeswax; and
   (b) an anionic emulsifier that is substantially hydrophilic and is soluble in water.

The carbohydrate polymer is typically selected from the group consisting of galactoarabinan, polygalactose, and polyarabinose. Preferably, the carbohydrate polymer is galactoarabinan.

The anionic emulsifier that is substantially hydrophilic and soluble in water can be selected from the group consisting of sodium lauryl sulfate, sodium laureth sulfate, sodium oleyl succinate, sodium dodecylbenzenesulfonate, and sodium lauryl sarcosinate. A particularly preferred anionic emulsifier is sodium lauryl sulfate.

The pH of the composition is adjusted to a range of between about 5.0 and about 6.5, typically with an acid. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of propylene glycol, glycerin or butylene glycol. Preferably, the solvent component is propylene glycol.

This embodiment of the invention can further comprise a chelator component. Preferably, the chelator component is tetrasodium ethylenediaminctetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

This embodiment of the composition can also include an antioxidant. A preferred antioxidant is butylated hydroxytoluene.

This embodiment of the invention can further comprise a preservative component. The preservative component can comprise one or more of methylparaben or propylparaben. Preferably, the preservative component comprises methylparaben and propylparaben.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention.

Water can comprise from about 50.0% to about 90.0% of this embodiment of the composition. Preferably, water comprises from about 60.0% to about 80.0% of this embodiment of the composition. An optimum concentration of water is about 61.65% of this embodiment of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Sodium lauryl sulfate, as a 30% solution, can comprise from about 0.50% to about 5.0% of this embodiment of the composition. Preferably, sodium lauryl sulfate, as a 30% solution, comprises from about 1.0% to about 3.0% of this embodiment of the composition. An optimum concentration of sodium lauryl sulfate, as a 30% solution, is about 1.90% of this embodiment of the composition.

Tetrasodium EDTA can comprise from about 0.05% to about 0.30% of this embodiment of the composition. Preferably, tetrasodium EDTA comprises from about 0.10% to about 0.20% of this embodiment of the composition. An optimum concentration of tetrasodium EDTA is about 0.15% of this embodiment of the composition.

Galactoarabinan can comprise from about 1.0% to about 25.0% of this embodiment of the composition. Preferably, galactoarabinan comprises from about 3.0% to about 15.0% of this embodiment of the composition. An optimum concentration of galactoarabinan is about 5.00% of this embodiment of the composition.

Citric acid can comprise from about 0.05% to about 0.25% of this embodiment of the composition. Preferably, citric acid comprises from about 0.10% to about 0.20% of this embodiment of the composition. An optimum concentration of citric acid is about 0.15% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 4.20% of this embodiment of the composition.

Stearyl alcohol can comprise from about 0.50% to about 6.0% of this embodiment of the composition. Preferably, stearyl alcohol comprises from about 1.0% to about 4.0% of this embodiment of the composition. An optimum concentration of stearyl alcohol is about 2.00% of this embodiment of the composition.

Beeswax can comprise from about 0.50% to about 5.0% of this embodiment of the composition. Preferably, beeswax comprises from about 1.0% to about 3.0% of this embodiment of the composition. An optimum concentration of beeswax is about 1.90% of this embodiment of the composition.

Cod liver oil can comprise from about 0.50% to about 15.0% of this embodiment of the composition. Preferably, cod liver oil comprises from about 1.0% to about 10.0% of this embodiment of the composition. An optimum concentration of cod liver oil is about 2.00% of this embodiment of the composition.

Butylated hydroxytoluene can comprise from about 0.1% to about 3.0% of this embodiment of the composition. Preferably, butylated hydroxytoluene comprises from about 0.25% to about 2.50% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Allantoin can comprise from about 0.50% to about 2.0% of this embodiment of the composition. Preferably, allantoin comprises from about 1.0% to about 2.0% of this embodiment of the composition. An optimum concentration of allantoin is about 1.50% of this embodiment of the composition.

If present, fragrance can comprise from about 0.05% to about 0.50% of this embodiment of the composition. Preferably, if present, fragrance can comprise from about 0.10% to about 0.40% of this embodiment of the composition. An optimum concentration of fragrance is about 0.20% of this embodiment of the composition.

Examples of particularly preferred compositions according to the present invention are described below.

The composition is prepared by standard mixing techniques, such as are conventional in the cosmetic art and in the art of over-the-counter drug formulation for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. The composition can be mixed in two or more batches, such as one batch containing lipid-soluble ingredients and another batch containing water-soluble ingredients, and the batches can then be mixed at the final stage of preparation.

The batches to be used are shown in Tables 1–11.

Compositions according to the present invention can be formulated for the treatment of skin diseases and conditions. Among the skin diseases and conditions for which compositions according to the present invention can be formulated are epidermolysis bullosa, decubitus ulcers, pressure ulcers, diabetic ulcers, and milia. Compositions according to the present invention can be formulated for treatment of other skin diseases and conditions. The details of the composition can be varied according to the particular condition to be treated. For example, greater or lesser degrees of oil or lipid-soluble components can be included, and, in the case of compositions intended to be used on patients who may undergo allergic reactions, compounds that often generate allergic reactions, such as fragrance and coloring, can be excluded. Such details can readily be ascertained by one of ordinary skill in the art.

The invention is illustrated by the following Examples. These Examples are for illustrative purposes only and are not intended to limit the invention.

EXAMPLE 1

Preparation of Skin Protectant Over-the-Counter Cream with pH of 7.4

Prior Art Example

A skin protectant over-the-counter (OTC) cream was prepared in accordance with the formulation of Table 1.

TABLE 1

COMPOSITION OF ALLANTOIN-CONTAINING SKIN CREAM WITH pH OF 7.4

| INGREDIENT | RANGE | PREFERRED | OPTIMUM |
|---|---|---|---|
| Part A | | | |
| Water | 50.0–90.0 | 55.0–75.0 | 66.20 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Part B | | | |
| Lanolin Oil | 5.0–15.0 | 8.0–12.0 | 10.60 |
| Cetyl Alcohol | 3.0–10.0 | 3.5–7.5 | 6.80 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was then added to the Part A mixture with mixing. The resulting mixture was then cooled to 120° F. with continued mixing. The Part C ingredients were then added with mixing. The final emulsion was allowed to cool with continued mixing. The resulting cream had a pH of 7.4. Samples of the cream prepared from Example 1 were used for accelerated aging stability studies and analyzed for their allantoin concentration after a period of time at 40° C. The results are shown in Table 2.

As can be seen from Table 2, the allantoin in the cream from Example 1 undergoes degradation and would not meet the specifications required for an OTC drug.

TABLE 2

STABILITY OF ALLANTOIN IN SKIN CREAM COMPOSITION OF EXAMPLE 1 WITH STORAGE AT 40° C.

| Days at 40° C. | Weight % Allantoin |
|---|---|
| 0 | 1.5 |
| 30 | 1.4 |
| 60 | 1.3 |
| 90 | 1.2 |

EXAMPLE 2

Preparation of a Cream Containing Allantoin with Lower pH

An OCT skin cream containing allantoin was prepared using the ingredients in Table 3 to provide a cream with a lower pH.

TABLE 3

COMPOSITION OF ALLANTOIN-CONTAINING SKIN CREAM WITH pH OF 5.3

| INGREDIENT | RANGE | PREFERRED | OPTIMUM |
|---|---|---|---|
| Part A | | | |
| Water | 50.0–90.0 | 55.0–75.0 | 68.68 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Citric Acid | 0.05–0.50 | 0.08–0.35 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.20 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was added to the Part A mixture with mixing. The resulting mixture was then cooled to 120° F. with mixing at which time the Part C ingredients were added with mixing. The final emulsion was allowed to cool with continue mixing. The resulting cream had a pH of 5.3.

It was found that a similar cream was produced if Part B was added to Part A or Part A was added to Part B. However, the cream has a better appearance if the oil phase and water phase are homogenized under high shear after the two phases are added to one another.

Samples of the cream of this example were used for accelerated aging stability studies and analyzed for their allantoin concentration. The results are shown in Table 4. As can be seen from Table 4, the allantoin is stable over time in a cream with a pH of 5.3.

TABLE 4

STABILITY OF ALLANTOIN IN SKIN CREAM COMPOSITION OF EXAMPLE 2 WITH STORAGE AT 40° C.

| Days at 40° C. | Weight % Allantoin |
|---|---|
| 0 | 1.4 |
| 30 | 1.4 |
| 60 | 1.4 |
| 90 | 1.4 |

EXAMPLE 3

Preparation of Allantoin-Containing Skin Cream with Ionic Emulsifiers

An allantoin-containing skin cream with ionic emulsifiers is prepared according to Table 5. The preparation follows the method used in Example 2, with the ingredients in each of Part A, Part B, and Part C being combined separately and then Part B being added to Part A, with Part C then being added to the combination of Part A and Part B. The pH is adjusted to a value in a range of from about 5.0 to about 5.8 by neutralizing the stearic acid with enough triethanolamine to reach this pH. Other bases can be used instead of triethanolamine.

TABLE 5

ALLANTOIN-CONTAINING SKIN CREAM WITH IONIC EMULSIFIERS

| INGREDIENT | RANGE | PREFERRED | OPTIMUM |
|---|---|---|---|
| Part A | | | |
| Water | 50.0–90.0 | 60.0–85.0 | 71.70 |
| Propylene Glycol | 2.0–9.0 | 4.0–7.0 | 5.70 |
| Triethanolamine (99%) | 0.20–4.0 | 0.50–3.0 | 1.25 |
| Part B | | | |
| Lanolin Oil | 5.0–15.0 | 8.0–12.0 | 10.60 |
| Cetyl Alcohol | 1.0–7.0 | 2.0–6.0 | 3.50 |
| Stearic Acid | 0.50–5.0 | 1.0–4.0 | 2.50 |
| Cod Liver Oil | 1.0–7.0 | 1.5–5.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

EXAMPLE 4

Preparation of Allantoin-Containing Skin Cream with Lactylate Emulsifiers

An allantoin-containing skin cream with the emulsifiers sodium stearoyl lactylate and sodium isostearoyl lactylate is prepared according to Table 6. The preparation follows the method used in Example 3. The pH is adjusted by the addition of the appropriate quantity of citric acid.

TABLE 6

ALLANTOIN-CONTAINING SKIN CREAM WITH LACTYLATE EMULSIFIERS

| INGREDIENT | RANGE | PREFERRED | OPTIMUM |
|---|---|---|---|
| Part A | | | |
| Water | 50.0–90.0 | 60.0–80.0 | 73.42 |
| Propylene Glycol | 2.0–9.0 | 4.0–7.0 | 5.70 |
| Citric Acid | 0.05–0.50 | 0.10–0.40 | 0.18 |
| Sodium Stearoyl Lactylate | 0.30–3.0 | 0.50–2.50 | 1.00 |
| Sodium Isostearoyl Lactylate | 0.05–1.0 | 0.10–0.70 | 0.25 |
| Tetrasodium EDTA | 0.05–0.25 | 0.10–0.20 | 0.15 |
| Part B | | | |
| Lanolin Oil | 5.0–15.0 | 8.0–12.0 | 10.60 |
| Cetyl Alcohol | 1.0–8.0 | 2.0–7.0 | 3.80 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

EXAMPLE 5

Preparation of Allantoin-Containing Skin Cream with Carboxypolymethylene Polymer An allantoin-containing skin cream with carboxypolymethylene polymer is prepared according to Table 7. The preparation follows the method used in Example 3, except that the triethanolamine (Part D) is added last, after the combining of Parts A, B, and C, to avoid thickening of the emulsion. The triethanolamine is added to adjust the pH.

TABLE 7

ALLANTOIN-CONTAINING SKIN CREAM WITH CARBOXYPOLYMETHYLENE POLYMER

| INGREDIENT | RANGE | PREFERRED | OPTIMUM |
|---|---|---|---|
| Part A | | | |
| Water | 50.0–90.0 | 60.0–80.0 | 73.55 |
| Carboxypolymethylene Polymer | 0.40–3.0 | 0.50–2.0 | 1.00 |
| Propylene Glycol | 2.0–9.0 | 4.0–7.0 | 5.70 |
| Part B | | | |
| Lanolin Oil | 5.0–15.0 | 8.0–12.0 | 10.00 |
| Cetyl Alcohol | 1.0–8.0 | 2.0–7.0 | 3.00 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |
| Part D | | | |
| Triethanolamine (99%) | 0.05–3.0 | 0.20–2.0 | 0.80 |

EXAMPLE 6

Preparation of Allantoin-Containing Skin Cream with Polyethylene Glycol Ethers of Cetearyl Alcohol An allantoin-containing skin cream with polyethylene glycol ethers of cetearyl alcohol is prepared according to Table 8. The preparation follows the method used in Example 3. The citric acid is added to adjust the pH.

TABLE 8

ALLANTOIN-CONTAINING SKIN CREAM WITH POLYETHYLENE GLYCOL ETHERS OF CETEARYL ALCOHOL

| INGREDIENT | RANGE | PREFERRED | OPTIMUM |
|---|---|---|---|
| Part A | | | |
| Water | 50.0–90.0 | 55.0–75.0 | 66.33 |
| Propylene Glycol | 2.0–9.0 | 4.0–7.0 | 5.70 |
| Tetrasodium EDTA | 0.05–0.50 | 0.10–0.30 | 0.15 |
| Ceteareth-25 | 0.50–4.0 | 2.00–3.50 | 2.60 |
| Citric Acid | 0.04–0.40 | 0.10–0.30 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.30 |
| Stearyl Alcohol | 1.0–5.0 | 2.0–4.0 | 3.50 |
| Ceteareth-6 | 0.50–4.0 | 1.0–3.0 | 1.80 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.50 | 0.10–0.30 | 0.15 |
| Allantoin | 0.50–2.0 | 1.0–2.0 | 1.50 |
| Fragrance | 0.05–0.50 | 0.10–0.30 | 0.20 |

EXAMPLE 7

Preparation of Allantoin-Containing Skin Cream with Polyethylene Glycol Ester of Stearic Acid and Glyceryl Stearate An allantoin-containing skin cream with a polyethylene glycol ester of stearic acid and glyceryl stearate is prepared according to Table 9. The preparation follows the method used in Example 3. The citric acid is added to adjust the pH.

TABLE 9

ALLANTOIN-CONTAINING SKIN CREAM WITH POLYETHYLENE GLYCOL ESTER OF STEARIC ACID AND GLYCERYL STEARATE

| INGREDIENT | RANGE | PREFERRED | OPTIMUM |
|---|---|---|---|
| Part A | | | |
| Water | 50.0–90.0 | 55.0–80.0 | 67.86 |
| Propylene Glycol | 2.0–9.0 | 4.3–7.0 | 5.70 |
| Tetrasodium EDTA | 0.05–0.50 | 0.10–0.30 | 0.15 |
| Citric Acid | 0.04–0.40 | 0.10–0.30 | 0.14 |
| PEG-100 Stearate | 1.0–5.0 | 1.5–3.0 | 2.60 |
| Part B | | | |
| Lanolin Oil | 5.0–15.0 | 2.0–12.0 | 10.60 |
| Cetyl Alcohol | 3.0–10.0 | 2.5–7.5 | 3.0 |
| Stearyl Alcohol | 1.0–4.0 | 1.0–3.5 | 2.50 |
| Glyceryl Stearate | 1.0–5.0 | 2.0–4.0 | 2.50 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.50 | 0.10–0.30 | 0.20 |
| Allantoin | 0.50–2.00 | 1.0–2.0 | 1.50 |
| Fragrance | 0.05–0.50 | 0.10–0.40 | 0.20 |

EXAMPLE 8

Preparation of Allantoin-Containing Skin Cream with Carboxypolymethylene Polymer and Polyethylene Glycol Ester of Stearic Acid An allantoin-containing skin cream with a carboxypolymethylene polymer and a polyethylene glycol ester of stearic acid is prepared according to Table 10. The preparation follows the method used in Example 5, with the triethanolamine (Part D) being added last. The triethanolamine is added to adjust the pH.

TABLE 10

ALLANTOIN-CONTAINING SKIN CREAM WITH A CARBOXYPOLYMETHYLENE POLYMER AND A POLYETHYLENE GLYCOL ESTER OF STEARIC ACID

| INGREDIENT | RANGE | PREFERRED | OPTIMUM |
|---|---|---|---|
| Part A | | | |
| Water | 50.0–90.0 | 60.0–85.0 | 69.95 |
| Carboxypolymethylene Polymer | 0.30–3.0 | 0.50–2.0 | 0.85 |
| Propylene Glycol | 2.0–9.0 | 4.0–7.0 | 5.70 |
| PEG-100 Stearate | 0.25–2.5 | 0.50–2.0 | 1.50 |
| Part B | | | |
| Lanolin Oil | 5.0–15.0 | 8.0–12.0 | 10.60 |
| Cetyl Alcohol | 1.0–8.0 | 2.0–7.0 | 4.20 |
| Stearyl Alcohol | 0.50–6.0 | 0.75–5.0 | 1.50 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.25 | 0.10–0.20 | 0.15 |
| Allantoin | 0.50–2.0 | 1.0–2.0 | 1.50 |
| Fragrance | 0.05–0.50 | 0.10–0.40 | 0.20 |
| Part D | | | |
| Triethanolamine (99%) | 0.05–3.0 | 0.20–2.0 | 0.80 |

EXAMPLE 9

Preparation of Allantoin-Containing Skin Cream with Galactoarabinan, Sodium Lauryl, Sulfate and Beeswax An allantoin-containing skin cream with galactoarabinan, sodium lauryl sulfate, and beeswax is prepared according to Table 11 The preparation follows the method used in Example 3. The citric acid is used to adjust the pH.

TABLE 11

ALLANTOIN-CONTAINING SKIN CREAM WITH GALACTOARABINAN, SODIUM LAURYL SULFATE, AND BEESWAX

| INGREDIENT | RANGE | PREFERRED | OPTIMUM |
|---|---|---|---|
| Part A | | | |
| Water | 50.0–90.0 | 60.0–80.0 | 61.65 |
| Propylene Glycol | 2.0–9.0 | 4.0–7.0 | 5.70 |
| Sodium Lauryl Sulfate (30%) | 0.50–5.0 | 1.0–3.0 | 1.90 |
| Tetrasodium EDTA | 0.05–0.30 | 0.10–0.20 | 0.15 |
| Galactoarabinan | 1.0–25.0 | 3.0–15.0 | 5.00 |
| Citric Acid | 0.05–0.25 | 0.10–0.20 | 0.15 |

TABLE 11-continued

ALLANTOIN-CONTAINING SKIN CREAM WITH
GALACTOARABINAN, SODIUM LAURYL SULFATE,
AND BEESWAX

| INGREDIENT | RANGE | PREFERRED | OPTIMUM |
|---|---|---|---|
| Part B | | | |
| Lanolin Oil | 5.0–15.0 | 8.0–12.0 | 10.60 |
| Cetyl Alcohol | 1.0–8.0 | 2.0–7.0 | 4.20 |
| Stearyl Alcohol | 0.50–6.0 | 1.0–4.0 | 2.00 |
| Beeswax | 0.50–5.0 | 1.0–3.0 | 1.90 |
| Cod Liver Oil | 0.50–15.0 | 1.0–10.0 | 2.00 |
| Butylated Hydroxytoluene | 0.10–3.0 | 0.25–2.5 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

ADVANTAGES OF THE PRESENT INVENTION

The present invention provides an allantoin-containing composition that is an oil-water emulsion using either an acidic anionic polymer and an anionic emulsifier or an acidic anionic polymer and a nonionic emulsifier that is an ethoxylated ether or ethoxylated ester. The composition can further include a carbohydrate polymer that can be polygalactose or polyarabinose. If an ethoxylated ether or ethoxylated ester is used, the composition can further comprise glyceryl stearate. The composition has improved thermal stability. The composition according to the present invention is useful for treatment of a number of skin diseases and conditions, including epidermolysis bullosa, pressure ulcers, diabetic ulcers, decubitus ulcers, and milia. Compositions according to the present invention are also useful as skin protectants even when these diseases are not present. Compositions according to the present invention are well tolerated and can be used with other treatments.

Although the present invention has been described in considerable detail, with reference to certain preferred versions thereof, other versions and embodiments are possible. Therefore, the scope of the invention is determined by the following claims.

I claim:

1. A composition comprising an oil-in-water emulsion comprising:
   (a) allantoin in a concentration of at least 0.50%;
   (b) at least one anionic or nonionic emulsifier that is hydrophilic and is soluble in water; and
   (c) a carbohydrate polymer selected from the group consisting of galactoarabinan, polygalactose, and polyarabinose;
   wherein the pH of the composition is in a range of from about 5.0 to about 5.8, the allantoin being stable in the emulsion for at least 90 days at 40° C.

2. The composition of claim 1 where the at least one anionic or nonionic emulsifier is selected from the group consisting of:
   (a) an acidic anionic polymer;
   (b) an anionic emulsifier selected from the group consisting of sodium lauryl sulfate, sodium laureth sulfate, sodium oleyl succinate, sodium dodecylbenzenesulfonate, and sodium lauryl sarcosinate;
   (c) a nonionic emulsifier that is an ethoxylated ether or an ethoxylated ester whose chain length ranges from 8 to 22 carbon atoms;
   (d) glyceryl stearate;
   (e) cetyl alcohol;
   (f) stearic acid;
   (g) sodium stearoyl lactylate;
   (h) sodium isostearoyl lactylate;
   (i) triethanolamine;
   (j) a polyethylene glycol ether of cetearyl alcohol wherein the number of polyethylene glycol moieties in the ether is from 6 to 40; and
   (k) beeswax.

3. The composition of claim 1 wherein the carbohydrate polymer is galactoarabinan.

4. A composition comprising an oil-in-water emulsion comprising:
   (a) allantoin in a concentration of at least 0.50%; and
   (b) an emulsifier system comprising:
      (i) an acidic anionic polymer; and
      (ii) a polyethylene glycol ester of stearic acid;
   wherein the pH of the composition is from about 5.0 to about 5.8, the allantoin being stable in the emulsion for at least 90 days at 40° C.

5. The composition of claim 4 wherein the acidic anionic polymer is a carboxypolymethylene polymer.

6. The composition of claim 4 further comprising a carbohydrate polymer.

7. The composition of claim 6 wherein the carbohydrate polymer is selected from the group consisting of galactoarabinan, polygalactose, and polyarabinose.

8. The composition of claim 7 wherein the carbohydrate polymer is galactoarabinan.

9. The composition of claim 4 wherein the composition further comprises at least one of:
   (a) an emollient component comprising at least one emollient selected from the group consisting of lanolin oil, cetyl alcohol, stearyl alcohol, and cod liver oil;
   (b) butylated hydroxytolutene;
   (c) a solvent component comprising at least one solvent selected from the group consisting of propylene glycol, glycerin, and butylene glycol; and
   (d) a preservative component comprising at least one preservative selected from the group consisting of methylparaben, propylparaben, and diazolidinyl urea.

10. The composition of claim 4 wherein the composition comprises:
    (a) from about 50.0% to about 90.0% of water;
    (b) from about 0.30% to about 3.0% of a carboxypolymethylene polymer;
    (c) from about 2.0% to about 9.0% of propylene glycol;
    (d) from about 0.25% to about 2.5% of PEG-100 stearate;
    (e) from about 5.0% to about 15.0% of lanolin oil;
    (f) from about 1.0% to about 8.0% of cetyl alcohol;
    (g) from about 0.5% to about 6.0% of stearyl alcohol;
    (h) from about 1.0% to about 7.0% of cod liver oil;
    (i) from about 0.10% to about 1.0% of butylated hydroxytoluene;
    (j) from about 0.10% to about 0.50% of methylparaben;
    (k) from about 0.10% to about 0.50% of propylparaben;
    (l) from about 0.05% to about 0.25% of diazolidinyl urea;
    (m) from about 0.50% to about 2.0% of allantoin;
    (n) from about 0.05% to about 0.50% of fragrance; and
    (o) from about 0.05% to about 3.0% of triethanolamine.

11. The composition of claim 10 wherein the composition comprises:

(a) from about 60.0% to about 85.0% of water;
(b) from about 0.50% to about 2.0% of a carboxypolymethylene polymer;
(c) from about 4.0% to about 7.0% of propylene glycol;
(d) from about 0.50% to about 2.0% of PEG-100 stearate;
(e) from about 8.0% to about 12.0% of lanolin oil;
(f) from about 2.0% to about 7.0% of cetyl alcohol;
(g) from about 0.75% to about 5.0% of stearyl alcohol;
(h) from about 1.0% to about 4.0% of cod liver oil;
(i) from about 0.20% to about 0.80% of butylated hydroxytoluene;
(j) from about 0.15% to about 0.40% of methylparaben;
(k) from about 0.15% to about 0.45% of propylparaben;
(l) from about 0.10% to about 0.20% of diazolidinyl urea;
(m) from about 1.0% to about 2.0% of allantoin;
(n) from about 0.10% to about 0.40% of fragrance; and
(o) from about 0.20% to about 2.0% of triethanolamine.

12. The composition of claim 11 wherein the composition comprises:
(a) about 69.95% of water;
(b) about 0.85% of a carboxypolymethylene polymer;
(c) about 5.70% of propylene glycol;
(d) about 2.0% of PEG-100 stearate;
(e) about 10.60% of lanolin oil;
(f) about 4.20% of cetyl alcohol;
(g) about 1.50% of stearyl alcohol;
(h) about 2.00% of cod liver oil;
(i) about 0.50% of butylated hydroxytoluene;
(j) about 0.30% of methylparaben;
(k) about 0.25% of propylparaben;
(l) about 0.15% of diazolidinyl urea;
(m) about 1.50% of allantoin;
(n) about 0.20% of fragrance; and
(o) about 0.80% of triethanolamine.

13. A composition comprising an oil-in-water emulsion comprising:
(a) allantoin in a concentration of at least 0.50%; and
(b) an emulsifier system comprising:
(i) an acidic anionic polymer; and
(ii) an anionic emulsifier that is hydrophilic and is soluble in water, the pH of the composition being ingested to a range of from about 5.0 to about 5.8, the allantoin being stable in the emulsion for at least 90 days at 40° C.

14. The composition of claim 13 wherein the anionic emulsifier is selected from the group consisting of sodium lauryl sulfate, sodium laureth sulfate, sodium oleyl succinate, sodium dodecylbenzenesulfonate, and sodium lauryl sarcosinate.

15. The composition of claim 14 wherein the anionic emulsifier is sodium lauryl sulfate.

16. The composition of claim 13 wherein the acidic anionic polymer is carboxypolymethylene.

17. The composition of claim 13 further comprising a carbohydrate polymer selected from the group consisting of galactoarabinan, polygalactose, and polyarabinose.

18. The composition of claim 17 wherein the carbohydrate polymer is galactoarabinan.

19. A composition comprising an oil-in-water emulsion comprising:
(a) allantoin in a concentration of at least 0.50%;
(b) an emulsifier system comprising:
(i) an acidic anionic polymer; and
(ii) a nonionic emulsifier that is an ethoxylated ether or an ethoxylated ester whose carbon chain length ranges from 8 to 22 carbon atoms, wherein the pH of the composition is from about 5.0 to about 5.8, the allantoin being stable in the emulsion for at least 90 days at 40° C.

20. The composition of claim 19 wherein the acidic anionic polymer is carboxypolymethylene.

21. The composition of claim 19 further comprising a carbohydrate polymer selected from the group consisting of galactoarabinan, polygalactose, and polyarabinose.

22. The composition of claim 19 wherein the carbohydrate polymer is galactoarabinan.

23. The composition of claim 19 wherein the emulsifier system further comprises glyceryl stearate.

24. The composition of claim 19 further comprising at least one of:
(a) an emollient component comprising at least one emollient selected from the group consisting of lanolin oil, cetyl alcohol, stearyl alcohol, and cod liver oil;
(b) butylated hydroxytoluene;
(c) a solvent component comprising at least one solvent selected from the group consisting of glycerin, propylene glycol, and butylene glycol; and
(d) a preservative component comprising at least one preservative selected from the group consisting of methylparaben, propylparaben, and diazolidinyl urea.

25. A composition comprising an oil-in-water emulsion comprising:
(a) allantoin in a concentration of at least 0.50%;
(b) a carbohydrate polymer; and
(c) an emulsifier system comprising:
(i) beeswax; and
(ii) an anionic emulsifier that is hydrophilic and is soluble in water;
wherein the pH of the composition is in a range from about 5.0 to about 6.5, the allantoin being stable in the emulsion for at least 90 days at 40° C.

26. The composition of claim 25 wherein the carbohydrate polymer is selected from the group consisting of galactoarabinan, polygalactose, and polyarabinose.

27. The composition of claim 26 wherein the carbohydrate polymer is galactoarabinan.

28. The composition of claim 25 wherein the anionic emulsifier that is substantially hydrophilic and soluble in water is selected from the group consisting of sodium lauryl sulfate, sodium laureth sulfate, sodium oleyl succinate, sodium dodecylbenzenesulfonate, and sodium lauryl sarcosinate.

29. The composition of claim 28 wherein the anionic emulsifier that is substantially hydrophilic and soluble in water is sodium lauryl sulfate.

30. The composition of claim 25 wherein the composition further comprises citric acid.

31. The composition of claim 25 further comprising at least one of:
(a) a solvent component comprising at least one solvent selected from the group consisting of propylene glycol, butylene glycol, and glycerin;
(b) an emollient component comprising at least one emollient selected from the group consisting of lanolin oil, cetyl alcohol, stearyl alcohol, and cod liver oil;
(c) butylated hydroxytoluene;

(c) tetrasodium EDTA; and
(d) a preservative component comprising at least one preservative selected from the group consisting of methylparaben and propylparaben.

32. The composition of claim 25 wherein the composition comprises:
(a) from about 50.0% to about 90.0% of water;
(b) from about 2.0% to about 9.0% of propylene glycol;
(c) from about 0.50% to about 5.0% of a 30% solution of sodium lauryl sulfate;
(d) from about 0.05% to about 0.30% of tetrasodium EDTA;
(e) from about 1.0% to about 25.0% of galactoarabinan;
(f) from about 0.05% to about 0.25% of citric acid;
(g) from about 5.0% to about 15.0% of lanolin oil;
(h) from about 1.0% to about 8.0% of cetyl alcohol;
(i) from about 0.50% to about 6.0% of stearyl alcohol;
(j) from about 0.50% to about 5.0% of beeswax;
(k) from about 0.50% to about 15.0% of cod liver oil;
(l) from about 0.1% to about 3.0% of butylated hydroxytoluene;
(m) from about 0.10% to about 0.50% of methylparaben;
(n) from about 0.10% to about 0.50% of propylparaben;
(o) from about 0.50% to about 2.0% of allantoin; and
(p) from about 0.05% to about 0.50% of fragrance.

33. The composition of claim 32 wherein the composition comprises:
(a) from about 60.0% to about 80.0% of water;
(b) from about 4.0% to about 7.0% of propylene glycol;
(c) from about 1.0% to about 3.0% of a 30% solution of sodium lauryl sulfate;
(d) from about 0.10% to about 0.20% of tetrasodium EDTA;
(e) from about 3.0% to about 15.0% of galactoarabinan;
(f) from about 0.10% to about 0.20% of citric acid;
(g) from about 8.0% to about 12.0% of lanolin oil;
(h) from about 2.0% to about 7.0% of cetyl alcohol;
(i) from about 1.0% to about 4.0% of stearyl alcohol;
(j) from about 1.0% to about 3.0% of beeswax;
(k) from about 1.0% to about 10.0% of cod liver oil;
(l) from about 0.25% to about 2.50% of butylated hydroxytoluene;
(m) from about 0.15% to about 0.40% of methylparaben;
(n) from about 0.15% to about 0.40% of propylparaben;
(o) from about 1.0% to about 2.0% of allantoin; and
(p) from about 0.10% to about 0.40% of fragrance.

34. The composition of claim 33 wherein the composition comprises:
(a) about 61.65% of water;
(b) about 5.70% of propylene glycol;
(c) about 1.90% of a 30% solution of sodium lauryl sulfate;
(d) about 0.15% of tetrasodium EDTA;
(e) about 5.00% of galactoarabinan;
(f) about 0.15% of citric acid;
(g) about 10.60% of lanolin oil;
(h) about 4.20% of cetyl alcohol;
(i) about 2.00% of stearyl alcohol;
(j) about 1.90% of beeswax;
(k) about 2.00% of cod liver oil;
(l) about 0.50% of butylated hydroxytoluene;
(m) about 0.30% of methylparaben;
(n) about 0.25% of propylparaben;
(o) about 1.50% of allantoin; and
(p) about 0.20% of fragrance.

\* \* \* \* \*